United States Patent [19]

Retzer

[11] 4,240,749
[45] Dec. 23, 1980

[54] TEST VESSEL

[75] Inventor: Erich Retzer, Maisach, Fed. Rep. of Germany

[73] Assignee: Compur-Electronic Gesellschaft mit beschränkter Haftung, Munich, Fed. Rep. of Germany

[21] Appl. No.: 950,866

[22] Filed: Oct. 12, 1978

[30] Foreign Application Priority Data

Oct. 25, 1977 [DE] Fed. Rep. of Germany ....... 7732771

[51] Int. Cl.³ ............................................. G01N 1/10
[52] U.S. Cl. ..................................... 356/246; 356/40
[58] Field of Search ........................ 23/230 R, 230 B; 356/246

[56] References Cited

U.S. PATENT DOCUMENTS 3,992,150  11/1976  Retzer ................................. 23/230 R
4,021,124   5/1977  Sardstedt ............................ 356/246

Primary Examiner—John K. Corbin
Assistant Examiner—B. Wm. de los Reyes
Attorney, Agent, or Firm—Stonebraker, Shepard & Stephens

[57] ABSTRACT

An account is given of a test vessel, more specially for use in a photometer. The vessel has inwardly running wall parts forming hollows and at the edges of these hollows there are outwardly running hollow processes for taking up capillary tubes used in conditioning a liquid in the vessel for a measuring operation.

7 Claims, 3 Drawing Figures

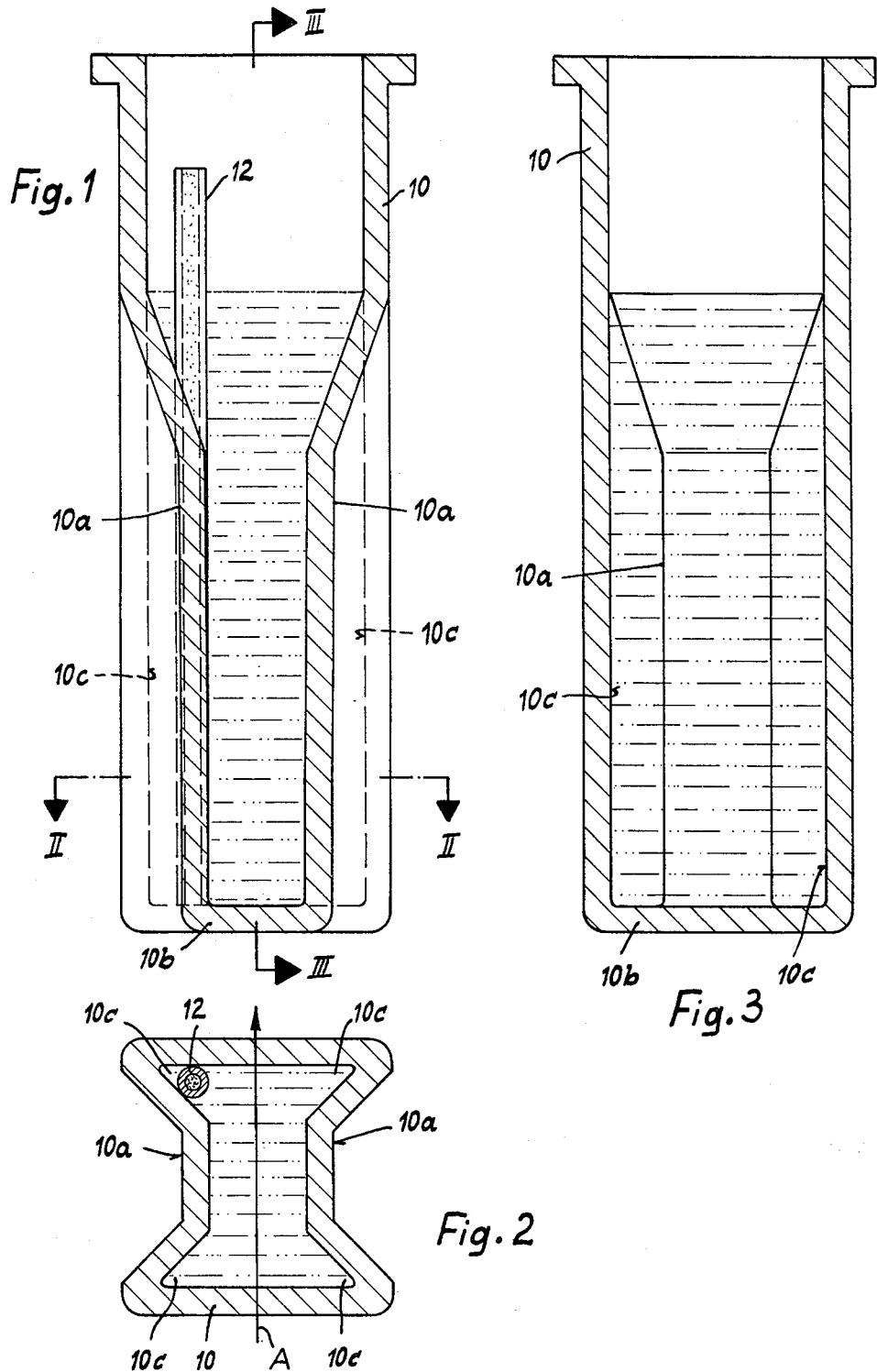

TEST VESSEL

BACKGROUND OF THE INVENTION (1) Field of the Invention

The invention relates to a test vessel with a four-cornered form and designed for taking up a sample to be measured with a photometer.

(2) The Prior Art

Earlier designs of such test vessels have been produced with hollows in their walls for producing a narrowed vessel cross-section for making certain that even samples of small size may be positioned in the way of the light of the photometer. In this respect the narrowed vessel cross-section is mostly hardly wider than the diameter of the measuring beam, so that its full width has to be free for the light to go through. So it is not possible for any part, decreasing the amount of light going through, to be placed in this cross-section when measuring is taking place, as for example capillary tubes, which are to be kept in the vessel even on measuring in a conditioning process of which there is an account in the German specification (Offenlegungsschrift) No. 2,422,260.

SHORT SUMMARY OF THE INVENTION

One purpose of the invention is that of making such development of a test vessel with a narrowed cross-section that a capillary tube may be kept in the vessel without any undesired effect even after the conditioning operation. In the invention the vessel may be so formed that the wall of the inwardly running hollow is furthermore formed limiting outwardly running hollow processes, placed along the same length of the vessel. In one of these hollow processes the capillary tube may be kept in the vessel even when the measuring operation is taking place, without any undesired effect being caused.

In the development of the vessel the design is such that one hollow is formed in each of two opposite walls, the hollow processes being placed at long sides of each hollow. In this respect the hollows and the hollow processes are placed running from the floor of the vessel upwards for a distance greater than half its height.

LIST OF FIGURES OF THE DRAWING

An account will now be given of one form of the invention using the accompanying drawing.

FIG. 1 is a section through the vessel in the length direction.

FIG. 2 is a cross-section on the line II—II of FIG. 1.

FIG. 3 is a section in the length direction on the line III—III of FIG. 1.

DETAILED ACCOUNT OF THE INVENTION

The test vessel 10 presented as one form of the invention has a four-cornered or rectangular form for all its length and is made of material transparent to light, more specialy plastics. Two opposite walls of the vessel 10 each have an inwardly running hollow 10a, which is furthermore made running from the floor 10b of the vessel to a level more than half way up. Because of this the volume of the vessel is decreased and at the same time it is made certain that after placing the vessel into the measuring apparatus, as for example a photometer, the light ray running in the direction of the arrow A (FIG. 2) of the measuring apparatus has to go through the whole width of the vessel 10 even though the vessel is made narrower.

The wall parts forming the two hollows 10a are designed forming outwardly running corner processes 10c. If on conditioning a liquid to be measured the steps are taken as noted in the German specification No. 2,422,260 and in this respect the reagent liquid is run in to the sample in the vessel 10 using a capillary tube 12, after the end of the mixing step this capillary 12 may be kept in one of the hollow processes 10c, because of the adhesion effect. This capillary tube is then clear of the measuring light ray and has no undesired effect on the measuring operation.

What is claimed is:

1. A test vessel with a four-cornered form over all its length and having for at least part of its length at least one inwardly running hollow in at least one wall part, said wall part forming the hollow being furthermore formed to provide an outwardly running hollow process, placed along the same length of the vessel as the hollow.

2. A test vessel as claimed in claim 1, characterised in that on two opposite wall parts of the vessel there is in each case one inwardly running hollow and to the long sides of these hollows there is in each case one hollow process running outwards.

3. A test vessel as claimed in claim 2, characterised in that the hollows and the processes are placed running from the floor of the vessel to a position more than half way up the vessel.

4. A test vessel for holding a quantity of liquid to be tested, said vessel having upright walls for confining liquid therein, said walls throughout a portion of the height of the vessel including, when viewed in horizontal cross-section, transparent front and rear walls substantially parallel to each other and arranged so that a testing ray may be projected through said front and rear walls and through the liquid between them, and side walls shaped to define a passage through which said ray may pass, said passage having a relatively narrow part at one point in the direction of travel of the ray and having a wider part at another point in the direction of travel of the ray, said wider part providing sufficient space to receive and retain a capillary tube in upstanding position and in a location where it will not be in the path of a ray of maximum width permitted by said narrow part.

5. The invention defined in claim 4, wherein at least one of said side walls meets at least one of said front and rear walls at an acute angle of substantially less than 90 degrees, the space within said acute angle consituting the space to receive and retain a capillary tube out of the path of said ray.

6. The invention defined in claim 4, wherein said shape of said side walls continues from the bottom of said vessel to a position more than half way up the height of the vessel.

7. The invention defined in claim 4, wherein said vessel is of generally square cross-sectional shape in the upper portion thereof, and wherein the lower portion of the vessel is formed with side walls which extend inwardly at an acute angle of substantially less than 90 degrees from the respective corner edges of the respective front and rear walls, for a substantial distance, and then continue in directions substantially perpendicular to the respective front and rear walls.

* * * * *